United States Patent [19]

Braun et al.

[11] Patent Number: 5,545,298

[45] Date of Patent: Aug. 13, 1996

[54] PROCESS FOR PREPARING POLYFLUOROCARBOXYLIC ACID CHLORIDES AND PERFLUOROCARBOXYLIC ACID CHLORIDES

[75] Inventors: Max Braun, Burgwedel; Werner Rudolph, Hanover; Kerstin Eichholz, Langenhagen, all of Germany

[73] Assignee: Solvay Fluor und Derivate GmbH, Hanover, Germany

[21] Appl. No.: 288,070

[22] Filed: Aug. 10, 1994

[30] Foreign Application Priority Data

Aug. 13, 1993 [DE] Germany .......................... 43 27 195.2
Dec. 14, 1993 [DE] Germany .......................... 43 42 601.8

[51] Int. Cl.$^6$ ................................................. C07B 33/00
[52] U.S. Cl. ................................. 204/157.6; 204/157.87; 204/157.89; 204/157.94; 562/541; 562/602; 562/605; 562/859
[58] Field of Search ............................ 204/157.6, 157.87, 204/157.89, 157.9; 562/541, 602, 605, 859

[56] References Cited

U.S. PATENT DOCUMENTS

| Re. 29,044 | 11/1976 | Konno et al. | 204/163 R |
|---|---|---|---|
| 2,736,695 | 2/1956 | Calfe et al. | 204/158 |
| 3,151,051 | 9/1964 | Braid et al. | 204/158 |
| 3,446,721 | 5/1969 | Scherer et al. | 204/158 |
| 3,674,664 | 7/1972 | Larsen et al. | 204/158 R |
| 3,725,475 | 4/1973 | Paucksch et al. | 260/544 F |
| 3,883,407 | 5/1975 | Dittman et al. | 204/158 R |
| 4,701,563 | 10/1987 | Franke et al. | 568/639 |
| 5,041,647 | 8/1991 | Gotoh et al. | 562/605 |
| 5,259,938 | 11/1993 | Huang | 204/157.87 |

FOREIGN PATENT DOCUMENTS

| 1069137 | 11/1959 | Germany . |
|---|---|---|
| 1254616 | 11/1967 | Germany . |
| 2418676 | 11/1974 | Germany . |

OTHER PUBLICATIONS

CA 82:97680 Dittman, "Trifluoroacetyl chloride."G. A. Wheaton et al., "Methyl Chlorodiflouroacetate...", *J. Fluorine Chem.*, vol. 8, pp. 97–100, (1976).
W. C. Francis et al., "Oxidation of Polyhalogeno–...", *J. Chem. Soc.* 1955, pp. 2151–2163.
R. N. Haszeldine et al., "Oxidation of Polyhalogeno–...", *J. Chem. Soc.* 1955, pp. 387–396.
E. O. Edney et al., "Chlorine Initiated Oxidation...", *J. Atmos. Chem.*, vol. 12, pp. 105–120, (1991).
Derwent Abstract of JP 04–210, 653.

*Primary Examiner*—John Niebling
*Assistant Examiner*—C. Delacroix-Muirheid
*Attorney, Agent, or Firm*—Evenson, McKeown, Edwards & Lenahan

[57] ABSTRACT

A process for preparing compounds corresponding to the formula RCFXC(O)Cl, in which X is fluorine or chlorine and R is fluorine or a perfluorinated C1- C10-alkyl group, preferably chlorodifluoroacetyl chloride, by photochemical oxidation of R122 ($CF_2ClCHCl_2$) and the preparation of trifluoroacetyl chloride by photochemical oxidation of R123 ($CF_3CHCl_2$) with oxygen under irradiation. The reaction is preferably carried out without pressurization and without addition of elemental chlorine.

8 Claims, No Drawings

PROCESS FOR PREPARING POLYFLUOROCARBOXYLIC ACID CHLORIDES AND PERFLUOROCARBOXYLIC ACID CHLORIDES

BACKGROUND OF THE INVENTION

The invention relates to a process for preparing polyfluorochlorocarboxylic acid chlorides and perfluorocarboxylic acid chlorides, particularly trifluoroacetyl chloride and chlorodifluoroacetyl chloride.

Polyfluorochloro- and perfluorocarboxylic acid chlorides are building blocks in chemical synthesis, for example for producing surfactants, pharmaceuticals and agrichemicals.

Chlorodifluoroacetyl chloride is an intermediate which can be used in a variety of ways in chemical synthesis. For example, it can be used in the production of dyes. Alkyl and aryl halides can be trifluoromethylated by a derivative of chlorodifluoroacetyl chloride, namely by the methyl ester, in the presence of potassium fluoride and copper iodide. Chlorodifluoroacetyl chloride has hitherto been prepared as described in U.S. Pat. No. 3,725,475, by solvolysis of $CF_2ClCCl_3$ with oleum or $SO_3$ in the presence of mercury compounds and chlorinated sulfur oxides. The aforementioned methyl ester is also a precursor for the preparation of difluorocarbene, see G. A. Wheaton, D. J. Burton in *J. Fluorine Chem.* 8 (1976), pages 97 to 100. Difluorocarbene is used in the production of insecticides, see U.S. Pat. No. 4,701,563. The preparation of difluorocarbene from PhHgCF_3 and other compounds of this type is problematical from an environmental standpoint.

Trifluoroacetyl chloride is likewise an important intermediate in chemical synthesis. The reaction with trifluoroethanol leads to the corresponding ester which can be cleaved by hydrogenation into two molecules of trifluoroethanol. Trifluoroethanol is a solvent which can be used in drying and cleaning processes.

The preparation of difluorochtoroacetyl chloride from 1,1-difluoro-1,2,2-trichloroethane and oxygen under photochemical irradiation by quartz lamps is described in Examined German Patent Application No. DE 1,069,137; in which chlorine is used as additive, although this leads to the formation of undesired byproducts.

SUMMARY OF THE INVENTION

It is an object of the present invention to provide a process for the preparation of polyfluorochloro- and perfluorocarboxylic acid chlorides, in particular of trifluoroacetyl chloride and chlorodifluoroacetyl chloride, which can be carried out without addition of mercury compounds and gives high yields at high reaction rates and high selectivity.

These and other objects are achieved by providing a process for preparing a compound corresponding to the formula RCFXC(O)Cl wherein X is fluorine or chlorine, and R is fluorine or a perfluorinated C1-C10-alkyl group, said process comprising reacting a starting compound corresponding to the formula $RCFXCHCl_2$ wherein R and X have the meanings defined above, with oxygen in the gas phase under activating irradiation, with the proviso that said reacting step is carried out without addition of elemental chlorine.

DETAILED DESCRIPTION OF PREFERRED EMBODIMENTS

According to the invention, compounds of the general formula RCFXC(O)Cl, in which X is fluorine or chlorine and R is fluorine or a perfluorinated C1- C10-alkyl radical, are prepared by reaction of $RCFXCHCl_2$, in which R and X are as defined above, with oxygen in the gas phase under activating irradiation, with the proviso that the reaction is carried out without addition of elemental chlorine. R is preferably C1- C3-alkyl (perfluorinated).

The process is preferably carried out at a pressure of from 1 to 10 atm. (abs.). It is very particularly preferred to carry out the process without pressurization. As used herein, the term "without pressurization" means that no additional pressure apart from the ambient pressure, the delivery pressure of the oxygen gas, (or the oxygen-containing gas) and any pressure generated by the HCl gas formed in the reaction, acts on the reaction mixture.

For example, 1,1,1,2,2-pentafluoro-3,3-dichloropropane can be converted into perfluoropropionyl chloride using the process of the invention. This compound can, for example, be used in the production of pharmaceuticals and agrichemicals.

The starting materials required are known and can be prepared by standard methods. The preparation of 1,1,1,2,2-pentafluoro- 3,3-dichloropropane from 1,1,1,2,2-pentafluoro- 3,3,3-trichloropropane and hydrogen over iridium catalysts is described, for example, in the Published Japanese Patent Application No. JP 04-210,653.

A particularly preferred embodiment relates to the preparation of trifluoroacetyl chloride and chlorodifluoroacetyl chloride.

This preferred embodiment comprises the preparation of compounds of the general formula $CF_2XC(O)Cl$, in which X is Cl, F, hence of trifluoroacetyl chloride and chlorodifluoroacetyl chloride, and is characterized in that 1,1-difluoro-1,2,2-trichloroethane (R122) or 1,1,1-trifluoro-2,2-dichloroethane is reacted with oxygen in the gas phase under activating irradiation without addition of elemental chlorine. The invention will be illustrated by means of this embodiment.

The activating radiation is preferably carried out using lamps which emit light which lies at least partly in the UV region. For example, high-pressure, intermediate-pressure and low-pressure Hg-vapor lamps are suitable. Suitable material for the corresponding apparatus components are UV-transparent material, for example quartz glass, if irradiation is carried out from outside.

The reaction is preferably carried out at a temperature of up to 200° C., particularly in the temperature range from 80° to 130° C. The molar ratio between the starting compound and oxygen ($O_2$) is preferably in the range from 1:1 to 1:20, in particular 1:1.1 to 1:3. Oxygen can be used in the form of oxygen-containing gas, e.g. as air, preferably as pure oxygen.

To protect the apparatus used, the condensation of reactants in the apparatus should be avoided if possible. It is also desirable in relation to the product purity, for as little as possible water to be present during the reaction. If desired, the reactants can be freed of entrained water in a known manner, for example by contacting them with drying agents such as drying beads or phosphorus pentoxide.

The continuous mode of operation is particularly preferred. In this, gaseous 1,1-difluoro-1,2,2-trichloroethane or 1,1,1-trifluoro-2,2-dichloroethane and oxygen are fed into the reaction vessel and product is continuously taken from the reaction vessel. Naturally, the amounts of starting compounds fed in and product taken out are relative to one another.

The average residence time in the reaction vessel is preferably between 0.1 and 30 minutes. The optimum average residence time, which is dependent, inter alia, on the lamp power and on geometric parameters of the irradiation apparatus, can be determined by means of simple tests and analysis of the product stream, e.g. by gas chromatography.

It has been found that better degrees of conversion and in particular higher selectivity can be achieved if, instead of a single irradiation lamp having a certain power, two or more lower-power lamps having the same total power are used in reactors arranged in series. Good turbulent mixing of the reaction mixture, e.g. by means of suitable baffles in the reactor, is also advantageous.

An advantage of the process of the invention is that polyfluoro- and perfluoroacetyl chlorides can be prepared with high selectivity.

The process of the invention allows, according to one variant, the preparation of chlorodifluoroacetyl chloride from 1,1-difluoro-1,2,2-trichloroethane without addition of chlorine under irradiation with oxygen in very high yield. According to a preferred embodiment, the reaction is carried out, as described above, without pressurization. This result has to be viewed as surprising. It is true that the oxidation of polyhalo compounds with oxygen under activating irradiation has already been described by the authors W. C. Francis and R. N. Haszeldine in *J. Chem. Soc.* 1955, pages 2151–2163 and by R. N. Haszeldine and F. Nyman in *J. Chem. Soc.* 1959, pages 387–396. However, in the experiments described by these authors, which were always carried out at elevated pressure, it was found that compounds containing the $CF_2Cl$ group decompose with formation of carbon dioxide and silicon tetrafluoride (reaction with the glass material of the reaction vessel). The high selectivity and high reaction rate of the photochemical oxidation of R122 without addition of chlorine could therefore not have been foreseen. The high yields obtained in the other variant of the invention, namely the preparation of trifluoroacetyl chloride, particularly when carried out without pressurization, also must be regarded as unexpected. This is because the hitherto prevailing view of those skilled in the art was that this reaction had to be carried out with addition of chlorine at elevated pressure (or at the superatmospheric pressure corresponding to the elevated temperature). Astonishingly, according to the process of the invention, even glass apparatus were not attacked. It is an advantage of the process of the invention that there is no formation of undesired byproducts which are otherwise formed with the addition of chlorine.

As has been established, chlorofluorocarbons may have regions of elevated danger of explosion at elevated pressure in the presence of oxygen. In contrast, the process of the invention allows hazard-free preparation of the acid halide.

The following examples are intended to illustrate the invention in further detail without limiting its scope.

EXAMPLE 1

Continuous preparation of chlorodifluoroacetyl chloride by photochemical oxidation of $CF_2Cl$-$CHCl_2$ (122) with oxygen.

In a 400 ml exchange-shaft photolysis reactor, a mixture of $CF_2Cl$-$CHCl_2$ (from pre-vaporizer a T=150° C.) and pure oxygen in a molar ratio of 1:2.2 was introduced in gaseous form at an internal reactor temperature of 100° C. with exclusion of moisture and without addition of chlorine and was simultaneously irradiated through quartz glass with a high-pressure Hg-vapor lamp TQ 718 from Heraeus (700 W). The condensation of the products leaving the reactor in gaseous form was carried out in a downstream condenser cooled to −60° C. (HCl and $COF_2$ removal). Over a period of 30 minutes, 155.9 g (920 mmole) of $CF_2ClCHCl_2$ were reacted. The conversion was 89%. The yield of chlorodifluoroacetyl chloride was 92.9% of theory (GC-percent) besides $COCl_2$, $CO_2$ and $COF_2$ as secondary components. A subsequent fine distillation via a 40 cm packed column gave, after taking off a forerun of $COCl_2$, pure chlorodifluoroacetyl chloride (bp. 27° C.). Recovered R122 was again metered into the prevaporizer using a pump.

EXAMPLE 2

Continuous preparation of trifluoroacetyl chloride by photochemical oxidation of $CF_3$-$CHCl_2$ (123) with oxygen.

In a 400 ml exchange-shaft photolysis reactor, a mixture of $CF_3$-$CHCl_2$ (from pre-vaporizer at T=100° C.) and pure oxygen in a molar ratio of 1:1.4 was introduced in gaseous form at an internal reactor temperature of 100° C. and without addition of chlorine and was simultaneously irradiated through quartz glass with a high-pressure Hg-vapor lamp TQ 718 from Heraeus (set to 500 W power). The products leaving the reactor in gaseous form were condensed in a downstream condenser cooled to −60° C. (HCl and $COF_2$ removal). Over a period of 30 minutes, 0.96 mole of $CF_3CHCl_2$ was reacted. The yield of trifluoroacetyl chloride (70% R123-conversion) was 93.2% of theory (GC-percent). $COCl_2$, $CO_2$ and $COF_2$ were detected as secondary components in the reactor gas. A subsequent fine distillation of the condensate in a packed column using intensive cooling gave pure trifluoroacetyl chloride (bp. −24.8° C.).

EXAMPLE 3

Example using increased lamp power.

The process was carried out as in Example 2, but using a lamp power of 700 W. The conversion of R123 in this case was 93%, the yield of trifluoroacetyl chloride was 84% (secondary components and workup as in Example 2) (GC-percent).

EXAMPLE 4

Example using a reduced ratio of R123:$O_2$.

The process was carried out as in Example 3, but using a 123/$O_2$ ratio of 1:0.6. The conversion of R123 was 58%, the yield of trifluoroacetyl chloride was 89% (GC-percent).

EXAMPLE 5

Example using an increased ratio of R123:$O_2$.

The process was carried out as in Example 3, but using a 123/$O_2$ ratio of 1:2.28. The conversion of R123 was 95%, the yield of trifluoroacetyl chloride was 85% (GC-percent).

EXAMPLE 6

Preparation of Perfluoropropionyl chloride.

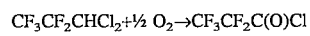

In a manner analogous to Example 1, a mixture of R225ca (98% purity; from a pre-vaporizer at T=130° C.) and pure oxygen in a molar ratio of 1: 1.7 was introduced in gaseous form into a reactor and simultaneously irradiated through quartz glass (Lamp setting 500 W;. The rate of introduction of R225ca was 0.45 mol/30 min. The selectivity for perfluoropropionyl chloride was 68%, and the conversion was 63%.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A process for preparing a compound corresponding to the formula

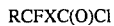

RCFXC(O)Cl wherein X is fluorine or chlorine, and R is fluorine or a perfluorinated C1- C10-alkyl group, said process comprising reacting a starting compound corresponding to the formula

RCFXCHCl$_2$ wherein R and X have the meanings defined above, with oxygen at a starting compound:oxygen molar ratio of 1:1.1 to 1:3 in the gaseous phase under activating irradiation, with the proviso that said reacting step is carried out without addition of elemental chlorine and without pressurization.

2. A process according to claim 1, for preparing a compound corresponding to the formula CF$_2$XC(O)Cl, in which X is Cl or F, wherein said starting compound is 1,1-difluoro-1,2,2-trichloroethane (R122) or 1,1,1-trifluoro-2,2-dichloroethane (R123).

3. A process according to claim 2, wherein said compound corresponding to the formula CF$_2$XC(O)Cl is trifluoroacetyl chloride.

4. A process according to claim 2, wherein said compound corresponding to the formula CF$_2$XC(O)Cl is chlorodifluoroacetyl chloride.

5. A process according to claim 1, wherein said reacting step is carried out at a temperature of up to 200° C.

6. A process according to claim 5, wherein said reacting step is carried out at a temperature in the range from 80° to 130° C.

7. A process according to claim 1, wherein said starting material is gaseous, and said process is carried out continuously by feeding the gaseous starting material and oxygen into a reaction vessel and continuously withdrawing the product from the reaction vessel, said reacting step being carried out with an average residence time in the reaction vessel of from 0.1 to 30 minutes.

8. A process according to claim 7, wherein said gaseous starting material is 1,1-difluoro-1,2,2-trichloroethane or 1,1,1-trifluoro-2,2-dichloroethane.

* * * * *